United States Patent [19]

Schaaf et al.

[11] 4,272,631

[45] Jun. 9, 1981

[54] HYDROLYSIS OF 5-(BETA-METHYLMERCAPTOETHYL)-HYDANTOIN

[75] Inventors: Kurt H. Schaaf, Clearwater, Fla.; Herman Horn, Staten Island, N.Y.

[73] Assignee: Diamond Shamrock Corporation, Dallas, Tex.

[21] Appl. No.: 124,295

[22] Filed: Feb. 25, 1980

[51] Int. Cl.³ .......................................... C07C 149/247
[52] U.S. Cl. ..................................... 562/559; 562/575
[58] Field of Search ................................ 562/559, 575

[56] References Cited

U.S. PATENT DOCUMENTS

| | | | |
|---|---|---|---|
| 2,527,366 | 10/1950 | Livak | 562/575 |
| 2,557,913 | 6/1951 | Livak | 562/559 |
| 2,557,920 | 6/1951 | White | 562/559 |
| 2,642,459 | 6/1953 | White | 562/575 |
| 3,636,098 | 6/1967 | Shima | 562/559 |
| 3,668,221 | 6/1972 | Shima | 562/575 |

FOREIGN PATENT DOCUMENTS 564129  9/1958  Canada .................................. 562/559

OTHER PUBLICATIONS

Holland, Chem. Soc., pp. 3403-3409 (1952).
Pierson, J. Am. Chem. Soc., 70 pp. 1450-1451 (1948).

Primary Examiner—Joseph E. Evans
Attorney, Agent, or Firm—Leslie G. Nunn, Jr.

[57] ABSTRACT

5-(Beta-methylmercaptoethyl)-hydantoin is hydrolyzed at superatmospheric pressure in an autoclave by heating in a mixture of (a) a hydroxide of a monovalent cation such as lithium, sodium, potassium, ammonium or alkyl substituted ammonium and (b) a hydroxide of a divalent cation such as calcium, barium or zinc.

12 Claims, No Drawings

HYDROLYSIS OF 5-(BETA-METHYLMERCAPTOETHYL)-HYDANTOIN

BACKGROUND OF THE INVENTION

1. Field of the Invention

This invention relates to the hydrolysis of 5-(beta-methylmercaptoethyl)-hydantoin to methionine.

2. Description of the Prior Art

U.S. Pat. No. 2,527,366—Livak et al—describe the hydrolysis of 5-(beta-methylmercaptoethyl)-hydantoin in an aqueous solution of barium hydroxide under pressure, e.g., a bomb or autoclave, at temperatures in excess of 115° C. but usually within the range of from 115° to 210° C. Patentees indicate that these conditions of temperature and pressure are not satisfactory for alkaline hydrolyzing agents in general. Their evaluation of ammonium hydroxide or lime as a hydantoin hydrolyzing agent under similar temperature and pressure conditions, either produced excessive by-products and the alpha-amino-monocarboxylic acid in an unsatisfactorily low yield or as a badly discolored amino acid which could not be satisfactorily decolorized. When barium hydroxide itself was tested as a hydrolyzing agent at atmospheric pressure, it was unsatisfactory. Hydrolysis occurred very slowly in a boiling mixture of the hydantoin and aqueous barium hydroxide at atmospheric pressure and the yield of alpha-amino-monocarboxylic acid was low.

Pierson et al, J. Am. Chem. Soc., 70, 1450 (1948), describe the hydrolysis of 17.4 g (0.10 mole) of 5-(beta-methylmercaptoethyl)-hydantoin by refluxing for six hours with a solution of 8.8 g of sodium hydroxide in 75 ml of water contained in a stainless steel flask. An additional 4.4 g of sodium hydroxide was then added and refluxing was continued for 24 hours. The reaction mixture was decolorized, neutralized to litmus with concentrated hydrochloric acid, and cooled to 5° C. to crystallize the methionine. A crude yield of 84.5% was obtained.

U.S. Pat. No. 2,557,913—Livak et al—disclose the hydrolysis of 5-(beta-methylmercaptoethyl)-hydantoin by heating in an aqueous solution of an alkali such as sodium carbonate, potassium carbonate, sodium hydroxide or potassium hydroxide. Hydrolysis with most alkalies results in a low yield or in discoloration. Barium hydroxide is preferred. Sufficient water to dissolve the major portion of the barium hydroxide is used and the hydrolysis mixture is heated in a closed bomb or autoclave at a temperature of from 115° to 210° C. Air is preferably swept from the reactor with nitrogen, steam or other inert gas prior to heating the mixture under pressure. Oxygen, if present during the hydrolysis, may cause by-product formation.

SUMMARY OF THE INVENTION

Alkaline hydrolysis of 5-(beta-methylmercaptoethyl)-hydantoin, by heating one mole of the hydantoin with a mixture of from about one mole to about eight moles of a hydroxide of a monovalent cation such as lithium, sodium, potassium, ammonium or alkyl substituted ammonium cation and from about one mole to about five moles of a hydroxide of a divalent cation such as calcium, barium or zinc cation in an aqueous medium containing from about 500 to about 5000 milliliters of water in an autoclave at superatmospheric pressure, produces methionine. Mixtures of equimolar quantities of the hydroxide of the monovalent cation and the hydroxide of the divalent cation are preferred.

DESCRIPTION OF THE PREFERRED EMBODIMENTS

Alkaline hydrolysis of 5-(beta-methylmercaptoethyl)-hydantoin by the following reaction produces methionine.

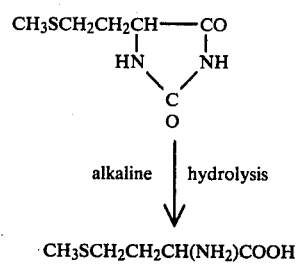

alkaline hydrolysis

CH$_3$SCH$_2$CH$_2$CH(NH$_2$)COOH

The hydantoin is hydrolyzed by heating an aqueous alkaline medium containing one mole of the hydantoin with from about one mole to about eight moles of a hydroxide of a monovalent cation such as lithium, sodium, potassium, ammonium or alkyl substituted ammonium and from about one mole to about five moles of a hydroxide of a divalent cation such as calcium, barium or zinc with from about 500 to about 5000 milliliters of water at superatmospheric pressure in an autoclave. Alkyl substituted ammonium cations include those having from one to four alkyl groups wherein each alkyl group may contain one to four carbon atoms. Alkyl substituted compounds such as monomethylammonium hydroxide, diethylammonium hydroxide, tripropylammonium hydroxide and tetrabutylammonium hydroxide may be used. The charge is then cooled and methionine recovered.

5-(Beta-methylmercaptoethyl)-hydantoin is a well known compound. It can be prepared from 3-methylmercaptopropionaldehyde, ammonium carbonate and potassium cyanide in 50% aqueous ethanol by the Buchrer procedure as described by Henze and Long in the Journal of the American Chemical Society, 63, 1936 (1941).

When sodium hydroxide and calcium hydroxide are used in the appropriate proportions in the hydrolysis, calcium ions react with the carbon dioxide, formed during the hydrolysis, and precipitate as calcium carbonate. Calcium hydroxide is inexpensive, so it is not necessary to recover calcium and the calcium carbonate can be discarded after its removal by filtration from the hydrolysis reaction mixture. The filtrate from the hydrolysis reaction mixture is principally a solution of the sodium salt of methionine from which methionine can be readily isolated.

The hydrolysis may be carried out at temperatures of from 105° to about 230° C. in an autoclave with the preferred temperatures being from about 125° to about 200° C.

For a fuller understanding of the nature and advantages of this invention, reference may be made to the following examples. These examples are given merely to illustrate the invention and are not to be construed in a limiting sense. All quantities, proportions, and percentages are by weight and all references to temperature are ° C. unless otherwise indicated.

EXAMPLE I

This example demonstrates the hydrolysis of 5-(beta-methylmercaptoethyl)-hydantoin with a mixture of sodium hydroxide and calcium hydroxide at superatmospheric pressure at 142° to 160° C.

Powdered calcium hydroxide (7.5 g of 99.5% purity; 0.10 mole) and 17.4 g (0.10 mole) of 5-(beta-methylmercaptoethyl)-hydantoin were added to a solution of 4.9 g of 98% sodium hydroxide pellets (0.12 mole) in 50 ml water, using another 50 ml water as rinsings. The mixture was charged into a rocking autoclave, heated to 142° C. over 65 minutes and maintained at 142°-160° C. at 57–102#/in$^2$ pressure for 70 minutes. At this time, the reaction mixture was quenched, washed out of the autoclave, and filtered with suction, using about 75 ml of water to wash the collected calcium carbonate.

The combined filtrates were then neutralized to pH 5.95 with concentrated hdyrochloric acid and concentrated in vacuo with stirring until methionine crystals separated. After the mixture had been stored at 5° C., it was stirred in an ice-water bath for 4 hours and filtered with suction. The methionine filter cake was washed with two 15 ml portions of water and dried in air at 50° to give 9.5 g of white, shiny crystals, m.p. 270° C./dec.

The combined mother-liquor and washings were then acidified to a pH of 1 with concentrated hydrochloric acid and evaporated to dryness in vacuo on the steam-bath. The residue, after drying in air at 50° C., was extracted with six 50 ml portions of refluxing methanol.

The combined extracts were filtered, and the filtrate was concentrated to 20 ml with intermittent hot filtrations to remove some salt which separated during the concentration. The 20 ml concentrate was filtered hot by gravity, using two 2.5 ml portions of hot methanol as rinsings.

The combined filtrates were treated with pyridine until neutral to Congo Red during which methionine crystals separated. After the mixture had been stored at 5° C., methionine crystals were collected, washed with methanol and dried in air at 50° C. to obtain 2.3 g of light-tan solids, m.p. 261° C./dec. Combined yield of methionine was 79.2% of theoretical.

EXAMPLE II

This example demonstrates the hydrolysis of 5-(beta-methylmercaptoethyl)-hydantoin with a mixture of sodium hydroxide and calcium hydroxide at superatmospheric pressure at 150° to 157° C.

The same quantities of reagents were used in this preparation as used in Example I, except that the mixture was heated to 150° C. in the rocking autoclave over a period of 55 minutes and maintained at 150°-157° C. at a pressure of 78–100#/in$^2$ for 2 hours and then quenched. After quenching, the cold reaction mixture was filtered with suction, using approximately 100 ml of water to wash the calcium carbonate precipitate. The combined filtrates were neutralized to a pH of 5.93 with concentrated hydrochloric acid and then concentrated in vacuo on the steam-bath until methionine crystals separated. The concentrated mixture was stirred at room temperature overnight and then in an ice-water bath for 5 hours. At this time, the methionine was collected, washed with two 10 ml portions of water, and dried in air at 50° C. to give 10.8 g of cream-colored solids, m.p. 270° C./dec.

The combined mother-liquor and washings from the filtration were acidified to a pH of 1 with concentrated hydrochloric acid and evaporated to dryness in vacuo on the steam-bath. After drying in air at 50° C., the residue was extracted with six 50 ml portions of refluxing methanol. The combined methanol extracts were processed in the same manner as described in Example I to give 1.8 g of pale-tan solids, m.p. 247° C./dec. Analysis of the solids showed it to contain 65.2% methionine and the combined yield of methionine was 80.5% theory.

EXAMPLE III

This example demonstrates the hydrolysis of 5-(beta-methylmercaptoethyl)-hydantoin with a mixture of sodium hydroxide and calcium hydroxide at superatmospheric pressure at 150° to 157° C.

Powdered calcium hydroxide (7.5 g of 99.5% purity; 0.10 mole) and 17.4 g (0.10 mole) of 5-(beta-methylmercaptoethyl)-hydantoin (m.p. 104°-108° C.) were added to a solution of 4.9 g of 98% sodium hydroxide pellets (0.12 mole) in 50 ml water, using another 50 ml water as rinsings. This mixture was charged into a rocking autoclave, heated at 150°-157° C. and 78–105#/in$^2$ pressure for 4 hours, and then quenched. After quenching, the cold reaction mixture was washed out of the autoclave with water and filtered with suction. The collected calcium carbonate was washed with water and dried to obtain 9.5 g of cream-colored solid (95% theory).

The combined filtrates from the filtration were then neutralized to pH 5.98 with concentrated hydrochloric acid and concentrated in vacuo with stirring until methionine crystals separated. After the mixture was stirred for 1 hour at room temperature and for 2.5 hours in an ice-water bath, it was collected by filtration with suction. The collected methionine crystals were washed with two 10 ml portions of water and dried in air at 60° C. to give 9.3 g of cream-colored methionine, m.p. 265° C./dec. (62.4% theory).

The combined mother-liquor and washings were acidified to a pH of 1 with concentrated hydrochloric acid and evaporated to dryness in vacuo on the steam-bath. The residue, after drying in air at 60° C., was extracted with five 50 ml portions of refluxing methanol.

The combined extracts were filtered, and the filtrate was concentrated to 80 ml and filtered hot to remove some inorganic salt, which were washed with two 10 ml portions of hot methanol. The combined filtrates were evaporated to dryness in vacuo on the steam-bath. The residue was refluxed with 25 ml methanol and the mixture filtered hot to remove further amounts of inorganic salts, using two 3 ml portions of hot methanol as rinsings. The combined filtrates from the residue were treated with pyridine until neutral to Congo Red during which methionine crystals separated. After the mixture had been stirred at room temperature for 2 hours and stored at 5° C. overnight, 2.6 g of cream-colored methionine crystals (m.p. 259° C./dec.) were isolated, equivalent to 17.5% theoretical yield. Combined yield was 79.9% theory.

EXAMPLE IV

This example demonstrates the hydrolysis of 5-(beta-methylmercaptoethyl)-hydantoin with a mixture of sodium hydroxide and freshly prepared zinc hydroxide at superatmospheric pressure at 150° to 156° C.

Zinc hydroxide was freshly prepared by dissolving 14.4 g (0.1 mole) of 95% pure zinc chloride in 75 ml of distilled water, and treating the zinc chloride solution with 20% sodium hydroxide solution in small portions until the mixture reacted neutral to pH paper. This mixture containing precipitated zinc hydroxide was digested on the steam-bath and treated with further small amounts of the base until slight alkalinity persisted. The precipitated zinc hydroxide was then collected and washed to neutrality.

The moist precipitated zinc hydroxide was quantitatively transferred to the reaction bomb using 100 ml of distilled water. Then 4.90 g (0.12 mole) of 98% sodium hydroxide pellets and 17.4 g (0.10 mole) of 5-(beta-methylmercaptoethyl)-hydantoin (m.p. 104°–107° C.) were added. The reaction mixture was heated in a rocking autoclave for 6 hours at 150°–156° C. and 78-135-#/in$^2$ pressure, and then quenched.

After quenching, the cold reaction mixture was washed out of the bomb with 250 ml distilled water, digested on the steam-bath for 2 hours, and filtered hot, using 150 ml hot water to wash the collected solids which were then discarded. The combined filtrates and washings from this filtration were concentrated to 100 ml in vacuo in a water-bath (75°–80° C.) during which a further small amount of solids separated. After the mixture had been filtered, the filtrate was neutralized to pH 6 with concentrated hydrochloric acid and stored at 5° C.

As no methionine separated, the solution was concentrated in vacuo until solids separated, and the mixture (about 80 ml) was stirred at room temperature for 3 hours and stored at 5° C. Methionine crystals were collected, washed with water, and dried at 60° C. to give 4.8 g of tan solids (m.p. 261° C./dec.), or 32.2% by theory.

The combined mother-liquor and washings were acidified to pH 1 with concentrated hydrochloric acid and evaporated to dryness in vacuo. The residue was extracted with five 50 ml portions of refluxing methanol. The combined, filtered extracts were evaporated to dryness in vacuo in a water-bath (75°–80° C.). Dried residue was refluxed with 25 ml methanol and filtered hot with suction, using two 5 ml portions of hot methanol to wash the collected, inorganic salts. Combined filtrates were concentrated to 25 ml and filtered hot by gravity.

The final filtrate was treated with pyridine until neutral to Congo Red. After treatment, the neutralized filtrate was stirred for 2 hours at room temperature, stored at 5° C. and then filtered to isolate 2.9 g of impure methionine (m.p. 235°–240° C./dec.) corresponding to a 19.4% yield of theory. Combined yield was 51.6% of theory.

EXAMPLE V

This example demonstrates the hydrolysis of 5-(beta-methylmercaptoethyl)-hydantoin with a mixture of ammonium hydroxide and calcium hydroxide at super-atmospheric pressure at 150° to 155° C.

A mixture of 17.4 g (0.10 mole) of recrystallized 5-(beta-methylmercaptoethyl)-hydantoin (m.p. 105.5° to 107° C.), 10.3 g (0.135 mole) of powered 97% calcium hydroxide, 50 ml distilled water and 12.0 g of 29% aqueous ammonium hydroxide (0.20 mole) was heated to 150° C. in a rocking autoclave over a period of 1.5 hours and maintained at 150°–155° C. for 8 hours, after which it was allowed to cool to room temperature overnight.

The reaction mixture was washed out of the bomb with 140 ml distilled water, stirred at room temperature for one hour, and filtered with suction using three 15 ml water to wash the precipitate. The combined, yellow filtrates were evaporated to dryness in vacuo on the steam bath yielding 16.5 g of light-yellow sticky solids. Dried residue was covered with 85 ml methanol and the mixture was digested on the steam bath for 30 minutes, cooled to room temperature and filtered with suction using three 10 ml portions of methanol as rinsings. The collected methionine was dried at 90°–95° C. overnight to give 2.87 g white solids (m.p. 256°–256.5° C./dec.; A.E.C. standard 257.5° C./dec.), or 19.3% of the theoretical yield.

Combined methanolic mother-liquor and washings were evaporated to dryness in vacuo on the steam bath, yielding 14.9 g dark yellow resin. It was dissolved in 55 ml water, and the solution was adjusted from pH 10.1 to pH 3.50 with 20% hydrochloric acid and then to pH 5.93 with 20% sodium hydroxide, during which crystals separated. The mixture was stirred at room temperature for about 2 hours and stored at 5° C. overnight.

The solids were collected, washed with two 5 ml ice cold water, and dried at 60°–68° C. over the weekend to give 6.06 g light tan solids (m.p. 258.5°–259° C./dec.; A.E.C. Standard 261.5°–262° C./dec.), equivalent to a 40.7% yield of methionine.

The combined mother-liquor and washings (at pH 5.75) were adjusted to pH 11.50 with 20% sodium hydroxide solution, during which a small amount of tan colored, flocculent material separated. The mixture was filtered with suction through a bed of Supercel, and the clear, yellow filtrate was added dropwise with stirring to a hot solution of 4.50 g ZnSO$_4$.H$_2$O in 25 ml water, during which zinc methionate precipitated. This mixture was digested on the steam bath for one hour, cooled to room temperature and filtered with suction, using two 10 ml water as washings. The dried (90°–95° C.) product amounted to 6.47 g of buff-colored solids; analysis of the material, gave the following results: 34.5% zinc, 32.4% methionine, 2.62% moisture, 61.8% ash. On this basis, the precipitate contained 2.1 g methionine, or 14.0% by theory. Combined yield of methionine amounted to 74.0% of the theoretical yield.

The calcium hydroxide-calcium carbonate precipitate, which had been collected from the original reaction mixture, was dried at 90°–95° C. overnight to give 10.85 g of buff-colored solids. Analysis showed that it contained less than 1% methionine.

EXAMPLE VI

This example demonstrates the hydrolysis of 5-(beta-methylmercaptoethyl)-hydantoin with a mixture of ammonium hydroxide and calcium hydroxide at super-atmospheric pressure at 150° to 157° C.

The same quantities of reactants and conditions were used in this preparation as in Example V, except that the reaction mixture contained 125 ml of water instead of 62 ml of water, was heated to 150° C. in the rocking autoclave and maintained at 150°–157° C. under pressure for 5 hours. Combined yield of methionine amounted to 70.1% of theory.

While the invention has been described with reference to certain specific embodiments thereof, it is understood that it is not to be so limited since alterations and changes may be made therein which are within the full and intended scope of the appended claims.

What is claimed is:

1. A process for preparing methionine from 5-(beta-methylmercaptoethyl)-hydantoin comprising hydrolzing at superatmospheric pressure in an autoclave at a temperature of from about 105° C. to about 230° C., one mole of the hydantoin with a mixture of from about one to eight moles of a hydroxide of a monovalent cation selected from the group consisting of lithium hydroxide, sodium hydroxide, potassium hydroxide, ammonium hydroxide and alkyl substituted ammonium hydroxide and from about one to about five moles of zinc hydroxide in an aqueous medium containing from about 500 to 5,000 milliliters of water per mole of the hydantoin and thereafter recovering methionine from the hydrolysis reaction mixture.

2. A process for preparing methionine from 5-(beta-methylmercaptoethyl)-hydantoin comprising hydrolyzing at superatmospheric pressure in an autoclave at a temperature of from about 105° C. to about 230° C., one mole of the hydantoin with a mixture of from about one to about eight moles of sodium hydroxide and from about one to about five moles of zinc hydroxide in an aqueous medium containing from about 500 to about 5,000 milliliters of water per mole of the hydantoin and thereafter recovering methionine from the hydrolysis reaction mixture.

3. The process of claim 1 wherein the hydrolysis is carried out at a temperature of from about 125° C. to about 200° C.

4. The process of claim 1 wherein about 1,000 to about 2,000 milliliters of water per mole of the hydantoin is present.

5. The process of claim 1 wherein the hydroxide of a monovalent cation is lithium hydroxide.

6. The process of claim 1 wherein the hydroxide of the monovalent cation is sodium hydroxide.

7. The process of claim 1 wherein the hydroxide of the monovalent cation is potassium hydroxide.

8. The process of claim 1 wherein the hydroxide of the monovalent cation is ammonium hydroxide.

9. The process of claim 1 wherein the hydroxide of the monovalent cation is an alkyl substituted ammonium hydroxide.

10. The process of claim 1 wherein equimolar quantities of the hydroxide of the monovalent cation and zinc hydroxide are present.

11. The process of claim 2 wherein equimolar quantities of the hydroxide of the monovalent cation and zinc hydroxide are present.

12. The process of claim 8 wherein equimolar quantities of the hydroxide of the monovalent cation and zinc hydroxide are present.

* * * * *